(12) United States Patent
Bronshtein (10) Patent No.: US 7,153,472 B1
(45) Date of Patent: *Dec. 26, 2006

(54) PRESERVATION AND FORMULATION OF BIOACTIVE MATERIALS FOR STORAGE AND DELIVERY IN HYDROPHOBIC CARRIERS

(75) Inventor: Victor Bronshtein, San Diego, CA (US)

(73) Assignee: Quadrant Drug Delivery Limited (GB)

( * ) Notice: Subject to any disclaimer, the term of this patent is extended or adjusted under 35 U.S.C. 154(b) by 506 days.

This patent is subject to a terminal disclaimer.

(21) Appl. No.: 10/130,840

(22) PCT Filed: Nov. 22, 2000

(86) PCT No.: PCT/US00/32071

§ 371 (c)(1),
(2), (4) Date: Dec. 13, 2002

(87) PCT Pub. No.: WO01/37804

PCT Pub. Date: May 31, 2001

(51) Int. Cl.
*B01J 19/00* (2006.01)
*A61L 11/00* (2006.01)
*A01N 1/02* (2006.01)

(52) U.S. Cl. .............................. 422/41; 422/1; 435/1.3; 435/243

(58) Field of Classification Search ..................... None
See application file for complete search history.

(56) References Cited

U.S. PATENT DOCUMENTS 5,766,520 A * 6/1998 Bronshtein .................. 264/4.6
6,872,357 B1 * 3/2005 Bronshtein et al. ........... 422/41

FOREIGN PATENT DOCUMENTS

| WO | WO 98 02240 | 1/1998 |
| WO | WO 98 16250 | 4/1998 |
| WO | WO 9816250 A1 * | 4/1998 |
| WO | WO 98 41188 | 9/1998 |
| WO | WO 9841188 A2 * | 9/1998 |

* cited by examiner

*Primary Examiner*—Michael G. Hartley
*Assistant Examiner*—Jake M. Vu
(74) *Attorney, Agent, or Firm*—Knobbe Martens Olson & Bear LLP (57) ABSTRACT

This invention relates to formulations comprising biological samples preserved as dry glassy powders and hydrophobic carriers, the formulations being adapted for the long-term storage and delivery of the bioactive materials, in particular viral and bacterial vaccines, vectors and cells, at ambient or higher temperatures, and to methods for preparing these formulations.

14 Claims, 2 Drawing Sheets

PRESERVATION AND FORMULATION OF BIOACTIVE MATERIALS FOR STORAGE AND DELIVERY IN HYDROPHOBIC CARRIERS

BACKGROUND OF THE INVENTION

1. Field of the Invention

This invention relates to formulations comprising biological samples preserved as glassy dry powders and hydrophobic, non-toxic carriers, the formulations being adapted for the long-term storage and delivery of the biological samples at selected ambient or higher storage temperatures, and to methods for preparing these formulations. More particularly, the invention relates to hydrophobic liquid formulations adapted for ambient or higher temperature storage and delivery of vaccines and vectors.

2. Description of the Related Art

Peptides, proteins, nucleic acids, hormones, antibodies and other biologically active molecules, viruses and bacteria, vectors, cells, and small multicellular specimens have a broad range of uses, including for example, human and veterinary pharmaceuticals, molecular biology, gene therapy, as well as in the food industries. Typically, these bioactive materials are active in aqueous environments; thus, conventional formulations of such samples have been in aqueous solutions. However, many bioactive materials are sensitive to degradation and loss of activity and/or viability in aqueous solutions, particularly at ambient or higher temperatures. Accordingly, bioactive materials often require refrigeration or have short shelf lives under ambient conditions. Further, many bioactive materials have only limited solubility in aqueous solutions. Even when they are soluble at high concentrations, they are prone to aggregation and precipitation.

Bioactive materials can degrade via a number of chemical mechanisms known in the art. Water is a reactant in nearly all of these degradation pathways. Further, water acts as a plasticizer, which allows unfolding and aggregation of proteins. Since water is a participant in almost all degradation pathways, reduction of the aqueous solution or suspension of bioactive materials to a dry powder provides an alternative formulation methodology to enhance the stability of such samples. Bioactive materials can be dried using various techniques, including freeze-drying, spray-drying and dessication. Aqueous solutions of bioactive materials are dried and stored as dry powders until their use is required.

A serious drawback to drying of bioactive materials is that often end uses of such materials require some sort of liquid form. Parenteral injection and the use of drug delivery devices for sustained delivery of drug are two examples of applications where one would like to use bioactive materials in a liquid form. For injection, dried bioactive materials must be reconstituted, adding additional steps which are time-consuming and where contamination may occur, and exposing the bioactive materials to potentially destabilizing conditions.

The sustained parenteral delivery of drugs provides many advantages. The use of implantable devices for sustained delivery of a wide variety of drugs or other beneficial agents is well known in the art. Typical devices are described, for example, in U.S. Pat. Nos. 5,034,229, 5,057,318 and 5,110,596. The disclosure of each of these patents is incorporated in its entirety herein by reference thereto.

Proteins are only marginally soluble in non-aqueous solvents, and such solvents typically unfold and denature proteins. Solubilization of native proteins in non-aqueous solvents typically requires derivatization or complexation of the protein. In attempting to achieve enzymatic catalysis in organic media, certain catalytic enzymes can be suspended in non-aqueous vehicles as powders, typically in hydrophilic organic solvents including alcohol ketones and esters. With enzyme hydration levels $\geq 10\%$ and/or the addition of low molecular weight protic compounds, these enzymes can have enough conformational mobility to exhibit appreciable enzymatic activity. Optimal activity levels are apparently achieved at enzyme hydration of approximately 30%. At a minimum, such enzymatic activity requires a level of "essential water" hydrating the protein. However, hydration levels (generally 10–40% w/w water/protein) and/or protic solvents, such as those used in these studies, typically result in unacceptable stability of proteins for pharmaceutical purposes. A further requirement for catalysis in non-aqueous solvents is that the enzyme be dried from a solution having a pH near the optimal pH for the enzymatic activity. This pH limitation is detrimental to storage of protein pharmaceuticals, because most protein degradation mechanisms are pH dependent, and it is often the case that proteins are most stable when dried at pH values far from the value where they exhibit bioactivity. Further, such catalytic enzyme systems are not amenable to the addition of protein stabilizers, particularly those that function by hydrogen bonding to the protein and reducing enzyme hydration (e.g., carbohydrates).

The field of gene therapy or gene transfer is advancing both experimentally and clinically. Nucleic acids have been transferred into cells using viral vectors such as adenovirus, retrovirus, adeno-associated virus, vaccinia virus, and sindbis virus, among others. Non-viral methods have also been used, including calcium phosphate precipitation, DEAE dextran, injection of naked DNA, electroporation, cochleates, cationic lipid complexes, liposomes, polymers (such as dendrimers and PLGA), virosomes, and the like.

DNA complexed with cationic lipids and/or liposomes has been shown to be an efficient means of transfecting a variety of mammalian cells. Such complexes are simple to prepare and may be used with a wide variety of DNA's and RNA's with little restriction to the size of nucleic acid. They have the ability to transfect many different cell types with efficiency and are not immunogenic. Current nucleic acid formulations, including DNA/liposome and RNA/liposome complexes, must be mixed shortly before administration, resulting in inconvenience in manufacture, shipping, storage and administration. Frequently, these two-part formulations are not very highly concentrated, requiring the administration of large volumes of solution. Dry powder formulations containing lyophilized nucleic acid/liposome complexes have also been used, but they require reconstitution with suitable aqueous solution just prior to administration. Aqueous complexes are inherently unstable and lose most, if not all, of their transfection activity within hours or a few days.

Consequently, there is a need for formulations of viral and bacterial vaccines and vectors, pharmaceutical materials, probiotics, and other industrially important bioactive materials that can overcome these limitations of the prior art. Such formulations should maintain the stability of the active materials, preferably at both room and body temperatures (25° and 37° C.), and exist in at least a flowable state for injection, pulmonary delivery, incorporation into delivery systems designed for immediate, delayed, or long term administration or other means of administration.

SUMMARY OF THE INVENTION

The present invention is related to a method of preparing a formulation for storage and delivery of a bioactive material which is sensitive to loss of bioactivity in aqueous solution at selected ambient or higher storage temperatures. The method comprises mixing the bioactive material with a protectant to form a solution or suspension, preserving the solution or suspension by foam formation to produce a mechanically stable, amorphous glass foam, milling the foam to yield a powdered composition, which at the selected ambient or higher storage temperatures, comprises solid, amorphous glass particles, and suspending the powdered composition in a hydrophobic, non-toxic vehicle.

In a preferred modes of the method, the bioactive material is selected from the group consisting of a lipid/DNA complex, a lipid/RNA complex, a virus, a virosome, a plasmid, cosmid, a circular piece of naked DNA, and a circular piece of naked RNA, a probiotic, a prokaryotic cell, and a eukaryotic cell.

The protectant in accordance with one mode of the present method, comprises one or more compounds selected from the group consisting of monosaccharides, disaccharides, oligosaccharides, their derivatives, and polymeric protectants. Preferably, the protectant comprises a mixture of a monosaccharide and a disaccharide. The monosaccharide may be a non-reducing derivative of a monosaccharide selected from the group consisting of fructose, glucose, sorbose, piscose, ribulose, xylulose, erythulose, and the like. The non-reducing derivative may be prepared from monosaccharides having at least one reducing group, wherein the at least one reducing group is modifying by methylation, ethylation, or chlorination. In one preferred mode to the method, the protectant comprises methyl α-d-lucopyranoside.

In variation of the method, the hydrophobic, non-toxic vehicle may be a liquid or a solid at ambient temperatures. In embodiments where the vehicle a liquid at ambient temperature, the vehicle may be selected from the group consisting of perhalohydrocarbons, unsubstituted saturated hydrocarbons, halogenated hydrocarbons, and esters thereof. More preferably, the vehicle is perfluorodecalin or cremophor EL.

In another aspect of the present invention, a formulation for storage and delivery of a bioactive material, is disclosed, wherein the formulation is made by the method described above. In one aspect, the formulation retains at least about 20% of the bioactivity for at least one month at 37° C. In another aspect, the formulation has a water content of less than about 10%.

The present invention is also related to vaccine formulations for ambient temperature storage and delivery of an infectious disease agent or part thereof which is sensitive to loss of activity in aqueous solution at selected ambient or higher storage temperatures. The vaccine formulation comprises a powdered composition including the infectious disease agent or part thereof and a protectant. The infectious disease agent may be selected from the group consisting of a virus, a bacteria, and a parasite. The powdered composition has a glass transition temperature higher that the ambient storage temperature and may comprise up to about 50% (w/w) of the vaccine formulation. The vaccine formulation also comprises a non-aqueous, non-toxic, hydrophobic vehicle, wherein the powdered composition is suspended in the vehicle at a concentration selected to yield a flowable suspension.

The protectant may be selected from the group consisting of sugars, polyols and polymers. More particularly, in accordance with another mode of the invention, the protectant further comprises a mixture including a monosaccharide and a disaccharide. Preferably, the monosaccharide is a non-reducing derivative of a monosaccharide selected from the group consisting of fructose, glucose, sorbose, piscose, ribulose, xylulose, erythulose, and the like. The non-reducing derivative may be prepared from monosaccharides having at least one reducing group, wherein the at least one reducing group is modifying by methylation, ethylation, or chlorination. In one preferred embodiment, the protectant comprises methyl α-d-glucopyranoside.

In one mode of the vaccine formulation, the infectious agent retains at least about 20% of the activity for at least one month at 37° C. The vaccine formulation preferably has a water content of the powdered composition of less than about 10%.

The non-aqueous, non-toxic, hydrophobic vehicle may be selected from the group consisting of perhalohydrocarbons, unsubstituted saturated hydrocarbons, halogenated hydrocarbons, and esters thereof. In one preferred mode, the vehicle is perfluorodecalin or cremophor EL.

In another mode of the present invention, a vector formulation is described for ambient temperature storage and delivery of a vector which is sensitive to loss of activity in aqueous solution at selected ambient or higher storage temperatures. The vector formulation comprises a powdered composition comprising the vector and a protectant. The vector is selected from the group consisting of a lipid/DNA complex, a lipid/RNA complex, a virus, a virosome, a plasmid, cosmid, a circular piece of naked DNA, and a circular piece of naked RNA. The powdered composition has a glass transition temperature higher that the ambient storage temperature and may comprise up to about 50% (w/w) of the vaccine formulation. The vector formulation also includes a non-aqueous, non-toxic, hydrophobic vehicle, wherein the powdered composition is suspended in the vehicle at a concentration selected to yield a flowable suspension.

The protectant may be selected from the group consisting of sugars, polyols and polymers. More particularly, in accordance with another mode of the vector formulation, the protectant further comprises a mixture including a monosaccharide and a disaccharide. Preferably, the monosaccharide is a non-reducing derivative of a monosaccharide selected from the group consisting of fructose, glucose, sorbose, piscose, ribulose, xylulose, erythulose, and the like. The non-reducing derivative may be prepared from monosaccharides having at least one reducing group, wherein the at least one reducing group is modifying by methylation, ethylation, or chlorination. In one preferred mode of the vector formulation, the protectant comprises methyl α-d-glucopyranoside.

In one mode of the vector formulation, the vector retains at least about 20% of the activity for at least one month at 37° C. The vector formulation preferably has a water content of the powdered composition of less than about 10%.

The non-aqueous, non-toxic, hydrophobic vehicle may be selected from the group consisting of perhalohydrocarbons, unsubstituted saturated hydrocarbons, halogenated hydrocarbons, and esters thereof. In one preferred mode, the vehicle is perfluorodecalin or cremophor EL.

The present invention also relates to a method of making a formulation for storage and delivery of a bioactive material which is sensitive to loss of bioactivity in aqueous solution.

The method comprises mixing the bioactive material with a protectant to form a solution or suspension. The solution or suspension is subjected to a vacuum which is sufficient to cause the solution or suspension to boil, wherein the boiling is continued until a mechanically stable foam is formed. The stable foam is dried under vacuum at a temperature above a desired storage temperature for a time that is sufficient to raise the glass transition temperature of the foam above the desired storage temperature. The bioactive material and protectant are vitrified by cooling. The foam is milled to yield a powdered composition, having a water content of less than about 10%. The powdered composition is suspended in a non-aqueous vehicle. The non-aqueous vehicle may be selected from the group consisting of perhalohydrocarbons, unsubstituted saturated hydrocarbons, halogenated hydrocarbons, and esters thereof, and more preferably, the vehicle is perfluorodecalin or cremophor EL.

In a variation to the method, the foam may be milled to yield a powdered composition prior to drying at a temperature above the desired storage temperature. The powdered composition is then vitrified by cooling.

Also described in relation to the method is a formulation for storage and delivery of a bioactive material, which is produced by the described method. In this formulation, the bioactive material may selected from the group consisting of a lipid/DNA complex, a lipid/RNA complex, a virus, a virosome, a plasmid, cosmid, a circular piece of naked DNA, and a circular piece of naked RNA, a prokaryotic cell, and a eukaryotic cell.

The protectant may be selected from the group consisting of sugars, polyols and polymers. In one mode, the protectant further comprises a mixture of a monosaccharide and a disaccharide. Preferably, the monosaccharide is a non-reducing derivative of a monosaccharide selected from the group consisting of fructose, glucose, sorbose, piscose, ribulose, xylulose, erythulose, and the like. The non-reducing derivative may be prepared from monosaccharides having at least one reducing group, wherein the at least one reducing group is modifying by methylation, ethylation, or chlorination. In one mode, the protectant used to produce the formulation in the described method is methyl α-d-glucopyranoside. In one variation of the formulation produced by the described method, the bioactive material retains at least about 20% of its bioactivity for at least one month at 37° C.

A unidose formulation of a vaccine is also disclosed as a variation of the present invention. The unidose formulation comprises a powdered glassy composition comprising a virus or bacteria, and a protectant comprising methyl α-d-glucopyranoside. The powdered glassy composition is suspended at a concentration selected to yield a flowable suspension in a non-aqueous vehicle selected from the group consisting of perhalohydrocarbons, unsubstituted saturated hydrocarbons, halogenated hydrocarbons, and esters thereof. The unidose vaccine formulation is placed in a prepackaged sterile syringe in an amount equivalent to a single effective immunizing dosage for a mammal. The vaccine is adapted to retain its activity for prolonged periods at high ambient temperatures.

DETAILED DESCRIPTION OF THE PREFERRED EMBODIMENT

A. Definitions

As used herein, the term "chemical stability" and/or "preservation" means that degradation of the biological material by chemical pathways such as oxidation, reduction, hydrolysis or enzymatic action, for example, does not exceed an acceptable level. In other words, at least a level of biological activity sufficient for the intended commercial application of the material is retained. In a preferred mode of the invention, a formulation is considered preserved if at least 20% of the biological activity is retained upon rehydration after storage for one week at 37° C.

The term "bioactive materials" encompasses peptides, polypeptides, proteins, enzymes and coenzymes, serums, vitamins, antibodies, and antibody fragments. Both naturally-derived or purified and recombinantly produced moieties are included in these terms. This term also includes lipoproteins and post-translationally modified forms, e.g., glycosylated proteins. Analogs, derivatives, agonists, antagonists and pharmaceutically acceptable salts of any of these are included in these terms. The term also includes modified, derivatized or non-naturally occurring peptides having D or L-configuration amino acids.

In a preferred mode of the present invention, the bioactive material is preserved by dehydration and mixed in a non-aqueous carrier to form a suspension that is adapted for ambient temperature storage and subsequent delivery to a mammal for the purpose of inducing immunity (i.e., antibody formation and/or specific cellular responses). Such a formulation is referred to as an "immunization". The bioactive materials suitable for use in an immunization include any antigenic substance, capable of inducing an immune response. More particularly, the antigen may be a protein or fragment thereof expressed on the extracellular domain of a tumor (e.g., for the treatment of cancer), an allergen, or a infectious agent of portion thereof (e.g., virus or bacteria). The term "vaccine" refers to a particular type of immunization, where the bioactive material is an infectious agent (or any part thereof), which is administered to a mammal to establish resistance to the infectious disease caused by the agent. Vaccines may include viruses, bacteria and parasites, viral particles and/or any portion of a virus or infectious disease agent or pathogen, including proteins and/or nucleic acids, which may be immunogenic and therefore useful in the formulation of vaccines.

In another aspect, the present invention also encompasses viral, bacterial and yeast-derived vectors (DNA and RNA), plasmids and cosmids, useful in transformation of cells. Such vectors may be used for gene therapy as well as molecular biology and genetic engineering. In another aspect, the term "bioactive materials" also includes any prokaryotic and eukaryotic cells, as well as certain small multicellular specimens.

The phrase "preservation by foam formation" refers to a scaleable procedure for drying sensitive biologics by boiling under vacuum under conditions wherein the biologics retain activity or viability for extended periods of time at ambient and higher temperatures. The specific methodological limitations encompassed by the phrase "preservation by foam formation" are detailed below, in two parts, (1) Primary Foam-Drying and (2) Stability Drying/Vitrification, and are disclosed in U.S. Pat. No. 5,766,520 to Bronshtein.

B. Preservation and Milling of Biological Materials Dehydration of biological specimens at elevated temperatures may be very damaging, particularly for example, when the temperatures employed for drying are higher than the applicable protein denaturation temperature. To protect the samples from the damage associated with elevated temperatures, the dehydration process may be performed in steps or by simultaneous increase in temperature and extent of dehydration. Primary dehydration should be performed at temperatures that are sufficiently low to permit dehydration without loss of biological activity. The preservation methods employed in accordance with the present invention are disclosed in U.S. Pat. No. 5,766,520 to Bronshtein and co-pending U.S. patent application Ser. Nos. 08/979,458 and 09/306,137, 09/589,381, 09/194,499 and 09/254,563, and co-pending U.S. Provisional Application Nos. 60/149,795, 60/166,928 and 60/161,204; the disclosures of which are herein incorporated in their entirety by reference thereto.

Protectants (fillers)—A variety of polyols and polymers are known in the art and may serve as protectants as long as they enhance the ability of the biologically active material to withstand drying and storage and do not interfere with the particular biological activity. Indeed, the protectant molecules provide other advantages during preservation (see infra, as an aid to generating mechanically stable foams) besides stabilizing biological materials during dehydration. More particularly, the protectants in accordance with the present invention may include, without limitation, simple sugars, such as sucrose, glucose, maltose, sucrose, xylulose, ribose, mannose, fructose, raffinose, and trehalose, non-reducing derivatives of monosaccharides and other carbohydrate derivatives, sugar alcohols like sorbitol, synthetic polymers, such as polyethylene glycol, hydroxyethyl starch, polyvinyl pyrrolidone, polyacrylamide, and polyethyleneamine, and sugar copolymers, like FICOLL and Dextran, and combinations thereof. Low molecular weight, highly soluble proteins may also serve as protectants.

In one preferred variation of the present invention, where cells, viruses, viral particles and/or viral and non-viral vectors are being preserved, the protective composition may further comprise mixtures of a low molecular weight sugar, a disaccharide, oligosaccharide and polymer including biological polymer. The low molecular weight sugar is used to penetrate and protect intracellular structures during dehydration. The low molecular weight, permeating sugars may be selected from a variety of ketoses, which are non-reducing at neutral or higher pH, or methylated or ethylated monosaccharides. Among the non-reducing ketoses, are included: the six carbon sugars, fructose, sorbose, and piscose; the five carbon sugars, ribulose and xylulose; the four-carbon sugar, erythulose; and the three-carbon sugar, 1,3 dihydroxydimethylketone. Among the methylated monosaccharides, are the alpha and beta methylated forms of gluco, manno, and galacto pyranoside. Among the methylated five carbon compounds are the alpha and beta forms of arabino and xylo pyranosides. Disaccharides, like sucrose, are known to be effective protectants during desiccation because they replace the water of hydration on the surface of biological membranes and macromolecules. In addition, sucrose and/or other fillers may be effectively transformed, by drying under vacuum, into stable foams, composed of thin amorphous films of the concentrated sugar.

Combining monosaccharides with disaccharides and oligosaccharides effectively prevents crystallization of the oligosaccharides during dehydration. In addition, a polymer may be employed to increase the glass transition temperature (Tg) of the dehydrated mixture, which may be decreased by inclusion of the low molecular weight monosaccharides. Any biological polymers that are soluble in concentrated sugar solutions may be employed. For example, polysaccharides, like FICOLL, and Dextran, and synthetic polymers, like hydroxyethyl starch, polyethylene glycol, polyvinyl pyrrolidone, polyacrylamide, as well as highly soluble natural and synthetic biopolymers (e.g. proteins) will help to stabilize biological membranes and increase Tg.

Primary Foam-Drying—To facilitate scale-up of the processing operations, preservation by foam formation involves the formation of a mechanically stable porous structure by boiling under a vacuum. The drying step is carried out at temperatures in the range of about −15 to 70 C. In one preferred embodiment, the sample temperature during the primary drying step is less than or equal to about 5° C. Preservation by foam formation is particularly well suited for efficient drying of large sample volumes, before vitrification, and as an aid in preparing a readily milled dried product suitable for commercial use. One advantage to foam-drying is that the process is scalable. Thus, the process may be applied for preservation of any volume of solution or suspension containing a sensitive bioactive material, from fractions of a milliliter (for analytical and optimization procedures) to hundreds of liters (for industrial scale production). Further details of preservation by foam formation are included in U.S. Pat. No. 5,766,520 by Bronshtein.

In a variation of the present invention, dilute biological samples may be concentrated by partially removing the water to form a more concentrated specimen before foam-drying under vacuum. This initial concentration step can be accomplished either before or after introduction of the sample into the processing chamber, depending on the concentration method chosen. Alternatively, some sample solutions or suspensions may be sufficiently concentrated after addition of the protectant molecules, and therefore not require any initial concentration. In situations where it is desirable to increase the concentration of the samples, methods contemplated for use in initial concentration include freeze-drying, evaporation from liquid or partially frozen state, reverse osmosis, other membrane technologies, or any other concentration methods known in the art.

The samples are subjected to vacuum, to cause them to boil during drying at temperatures substantially lower than 100 C. When reduced pressure is applied to the solutions or suspensions containing biologically active materials, these solutions or suspensions foam during boiling, and during the foaming process further solvent removal causes the ultimate production of a mechanically-stable open-cell or closed-cell porous foam. The mechanically stable porous structure, or foam, consists of thin amorphous films of the concentrated fillers.

While low vacuum pressures (in the range of 0.1–0.9 atm) may be applied to facilitate the initial evaporation to produce a concentrated solution, much higher vacuum pressures (0–24 Torr) are used to cause boiling. The vacuum for the boiling step is preferably 0–10 Torr, and most preferably less than about 4 Torr. Boiling in this context means nucleation and growth of bubbles containing water vapor, not air or other gases. In fact, in some solutions, it may be advantageous to purge dissolved gases by application of low vacuum (about 0.1–0.9 atm) at room temperature. Such "degassing" may help to prevent the solution from erupting out of the drying vessel. Once the solution is sufficiently concentrated, high vacuum can be applied to cause controlled boiling or foaming. Concentration of the protectant molecules recited above, in the range of 5–70% by weight, during initial evaporation aids in preventing freezing under subsequent high vacuum and adds to the viscosity, thereby facilitating foaming while limiting uncontrolled eruptions.

Rapid increases in pressure or temperature could cause a foam to collapse. Surfactants may optionally be added as long as those additives do not interfere with the biological activity of the solute intended for conversion to dry form. Moreover, drying of the protectant polymers also contributes to the mechanical stability of the porous structures. Foams prepared according to the present invention may be stored in the processing chamber under vacuum, dry gas, like $N_2$ atmosphere and/or chemical desiccant, prior to subsequent processing operations, (e.g. stability drying, vitrification or milling).

Stability Drying/Vitrification—The mechanically stable foams formed during primary drying, may undergo secondary or "stability" drying at increased temperatures. Since glass transition temperature (Tg) is dependent on the water content of the sample and since Tg increases with increased dehydration, different stability drying protocols may be applied depending on the desired storage temperature, to generate a Tg consistent with vitrification upon cooling to that storage temperature. However, because dehydration of materials is practically impossible once they have entered the glass state, the key to vitrification according to the present invention, where ambient storage temperatures may be desired, is to conduct the stability drying at a temperature significantly higher than the ambient temperature.

Ultimate storage temperatures are preferably within the range of 0–70 C. More preferably, common storage temperature selections are greater than or equal to 0, 4, 20, 40, and 50 C. In some cases, where refrigerated storage may be preferred, stability drying could be carried out at room temperature followed by cooling to the storage temperature or below. In other instances, however, where stability at room temperature is desired, dehydration at a temperature above room temperature should be employed, followed by cooling to room temperature.

For any given specimen to be preserved, the nature and stability characteristics of the specimen will determine the maximum temperature it can withstand during the primary drying step. In the case of enzyme preservation, it was shown that after primary drying at room temperature the stability drying temperature may be increased up to 50 C without loss of enzymatic activity. Then, the dehydration process can be continued during stability drying at higher temperature. Thus, by continuous or step-wise increases in the dehydration temperature, labile proteins can be placed in a state of thermal stability at temperatures well above their denaturation temperature.

In addition to conducting the stability drying at a temperature above the selected storage temperature, it is critical that this drying is carried out for a period of time sufficient to actually raise Tg above the storage temperature. Based on empirical results obtained with dried 10 μl drops of 15% sucrose+15% raffinose solution, it was demonstrated that more than 12 hours of stability drying at temperatures above 70 C was required to raise Tg to above 25 C. Primary drying in these experiments was for 12 hours at room temperature (20 C). The results suggest that extended stability drying times (more than 12 hours at 70 C and more than 60 hours at 50 C) may be needed to effect increases in Tg over room temperature. For some biological materials which are not heat labile, primary drying at higher temperatures, would reduce the stability drying time at elevated temperatures needed to increase Tg to above the selected storage temperature.

In one embodiment of the present invention, the foam is cooled from stability drying down to the milling temperature, milled, and then the powder is subjected to further drying either under vacuum or at atmospheric pressure. The subsequent drying temperature may be in the range of about 0° to 100° C. Such drying may be continued until the glass transition temperature is raised above a selected storage temperature within the range of about 0 to 70 C.

To ensure that the Tg is actually greater than the storage temperature, at least two methods are known for estimating Tg by thermal analysis. Differential scanning calorimetry (DSC) is the most commonly used technique. However, the Inventor has found that DSC may be unreliable for measuring Tg in samples that contain polymers. Alternatively, Thermally Stimulated Polarization (TSP) methods are specifically adapted for analysis of polymers. The TSP method is preferred because it is reliable for all samples, although it requires slightly larger sample volumes.

Formation of a Uniform Powder—Crushing means in accordance with the present invention includes conventional mills, homogenizers and sonicators, as well as other means for reducing the stable foam to a powder. These other means may include the physical deformation of a second container placed inside the drying chamber. The second chamber may be semirigid, wherein the foam is powdered by physical blows to the container or may be flexible, like a bag, wherein the foam is powdered by crushing or other physical deformation. Alternatively, preservation may take place within grid cells in a partitioned tray, wherein the foam may be scraped from the grid and crushed. The various crushing means are described in greater detail below.

1. Conventional Milling—Conventional milling methods and components may be used in accordance with the present invention. These include without limitation: brush mills; rotating blade mills as described in U.S. Pat. No. 5,352,471, incorporated herein by reference; pulverizing mills as described in U.S. Pat. No. 4,651,934, incorporated herein by reference; rotary attrition mills described in U.S. Pat. No. 4,404,346, incorporated herein by reference; jet mills, for example, of the type of the spiral or counter-pipe mills (CF Winnacker, Kucher; *Chemische Technologie,* 4th Edition, Volume 1, p. 91–93, 1984) as described and improved in U.S. Pat. No. 4,917,309, incorporated herein by reference; incremental cutting action mills, for example, a COMITROL® 1700 Mill, as described in U.S. Pat. No. 5,520,932, incorporated herein by reference; ball mills; hammer mills (e.g. MIKROPULVERIZER®); rotary tubular mills containing impact resistant metal balls, metal cylinder or bars or stones, for example, the micronizing mill described in U.S. Pat. No. 5,174,512, incorporated herein by reference; homogenizers; sonicators; and mills containing wires, like a weed-whacker; and any other milling means known in the art. The differences and advantages of the various types of mills, grinders and crushing mechanisms are well known to those of ordinary skill in pharmaceutical manufacturing techniques.

2. Deformable Container—There are a number of alternative approaches that can be taken to implement the concept of drying and reducing to a powder in the same drying chamber. A variation from conventional milling uses a second container placed inside the drying chamber. This second container would serve as the holder of the process fluid that is to be preserved via foam formation. The container would be placed in the chamber and filled with the preservative solution. This filling could be accomplished via a separate filling tube. Subsequent to the completion of preservation by foam formation, this same container could be sealed and withdrawn from the drying chamber and serve as either a final container or an intermediate container for further processing. Sealing could be accomplished via a simple capping device for semirigid containers or via heat sealing for flexible containers. In addition, if the container is semirigid, the mechanically stable foam contained within may be broken up in a kind of coarse milling, via a series of impacts of the container wall to a hard inflexible surface, or vice versa. If the container is flexible, as with a gas-permeable Lyoguard® bag, the foam contained within it may be coarsely milled by crushing the bag, using a relatively weak force. This could be accomplished with a simple roller device. Once coarsely broken up, the resulting particles may be either considered to be in finished form or, depending upon end use requirements, processed further by transferring to a milling machine. Since at this point the material would be in particle form, this transfer would be effected easily by gravity or vacuum devices commonly used in powder handling systems. The final milling would be performed by commercially available milling equipment and conducted in such a way as to mill the material to a particular particle size distribution as dictated by material final specifications. A Quadro Comil®, for example, would be suitable for this purpose.

Since the secondary container would be in a vacuum environment during preservation by foam formation, the transfer of heat to the preservation solution inside could be slow and difficult to control. This limitation could be overcome by using the concept of inductive heating. An induction coil wound around the exterior of the chamber would provide the heating source by inducing molecular motion in ionic species in the preserving solution. A bag holding device, or cassette, which would slide into and out of the drying chamber to provide for easier loading and unloading of the product could also serve as the device which would support the induction coil. Alternatively, the cassette could serve as the housing for more traditional heat transfer systems such as electrical resistance heating and recirculatory fluid heating. In order to provide for more uniform processing of the preservation solution, the cassette holding the container could also be made to rotate. In addition or in the alternative, electromagnetic or electrostatic inductive heating may be employed, as described in co-pending U.S. patent application Ser. No. 09/589,381.

The concept of a second container provides a number of advantages beyond those already identified above. In particular for aseptic processing, the filling tube, chamber and the container could be pre-sterilized by commonly accepted practice (e.g., irradiation, vaporous hydrogen peroxide (VHP), steam, etc., depending on the materials of construction of the respective items). This approach, coupled with the sealing devices described above, provides for a barrier-type of processing, thus effectively isolating the operator and product from each other during the course of preservation by foam formation. This is highly desirable for handling biological and toxic materials. The use of isolation or barrier technology is becoming the standard design approach for processing such materials in the pharmaceutical industry.

A product (now called Lyoguard®) developed by W. L. Gore for bulk lyophilization in an aseptic manner was also tested for its utility as an insert, deformable container in the process of preservation by foam formation. The Lyoguard® lyophilization bag was a heat sealable flexible bag consisting of one side that was a plastic that was not permeable to water vapor and another side consisting of a Gore-Tex® membrane. This membrane is an expanded polytetrafluoroethylene (PTFE), nominally 0.2 micron pore size, hydrophobic and not permeable to liquid water, but permeable to water vapor.

Because the Lyoguard® bag can pass water vapor while still preventing product in the liquid state from penetrating the membrane and leaking out, it provided an ideal way to process pharmaceutical products which in general require sterility. The basic method could also be applied to animal health products, probiotics, food, etc. In short, any product for which closed container processing might have an advantage in the areas of sterility, ease of handling, isolation of pathogens (e.g., bacteria and viruses) from the operators and extraneous particle contamination control could potentially benefit from application of the Lyoguard® bag to preservation by foam formation. In addition the flexible nature of the bag enhances the contact of the bag with the dryer shelf. Since the shelf is the heat transfer surface in a conventional freeze dryer, heat transfer should be optimal when conducting preservation by foam formation with the Lyoguard® bag. This could lead to faster drying cycles.

A series of experiments were initiated to investigate the possibilities of using the Lyoguard® Gore-Tex bag for preservation by foam formation. A 50% solution w/w with de-ionized water served as the testing media. A volume of 200 ml was filled into a 10×14 inch Lyoguard® bag. The bag was then heat-sealed using a commercially available heat-sealing device. Next the bag was placed on the one of the 3 shelves of a Virtis Genesis® lyophilizer which was custom-modified for preservation by foam formation. Boiling and eventually foam formation were observed through the semi-transparent lower impermeable membrane of the bag as drying proceeded. After overnight drying at 40° C., the bag was removed from the lyophilizer and examined. Mechanically stable foam appeared to have formed. This dried foam was brittle and easily crushed into small particles in the bag without opening the bag. This indicated that the bag could also function as a container for coarse milling of the foam product. Within approximately 30 minutes the bag was opened and about 1 L of water was added to observe the reconstitution character of the dried particles. Most of the particulate easily dissolved in less than 10 seconds. Subsequent test protocols involving altered pressure and temperature ramps and fills ranging from 200 to 400 ml in the 10×14 inch bag suggested that about 300 ml was the optimal fill level. At the completion of a typical run the appearance of the bag shows complete formation of foam and all of the material in the bag redissolves easily.

Bulk lyophilization of industrial enzymes, foods and pharmaceuticals is commonly done by utilizing stainless steel trays, which are placed on the temperature controlled shelves of the lyophilizer. The trays are typically filled in an appropriate environment for the particular product of interest and transported to the freeze dryer, whereupon they are loaded into the dryer and the lyophilization cycle is run. Tray dimensions and capacity are largely determined by the shelf area of the lyophilizer, the allowable fill height for the product and the material handling characteristics desired. For preservation by foam formation, the basic operation would be the same. Product is prepared according to the previous examples, poured into standard lyophilization trays and preserved by foam formation in a machine configured to meet the required conditions. The tray could be constructed of any material that would allow the transfer of heat from the product shelf to the product contained within the tray. Examples of suitable materials are stainless steels, coated steels, non-ferrous alloys such as aluminum and titanium and plastics such as polypropylene, polyethylene and the like. It is recognized that plastics will transfer heat less efficiently, but may have other offsetting advantages.

Because of certain aspects of preservation by foam formation, a number of innovations described herein are necessary to the typical lyophilization tray in order for it to perform properly in the production of a mechanically stable, dry foam. In a preferred embodiment the tray would be fitted with a grid structure located in the internal space defined by the tray bottom and sides. This grid structure would essentially divide the area of the tray into a series of cells of equal or unequal area such that the entire tray would be sectioned into smaller units. The function of the grid would be to reduce the area available for expansion of the foam during preservation by foam formation, thereby containing foam bubbles inside the area of each grid. This effectively reduces the height to which a foam structure can grow, thus minimizing the chance that the growing foam will contact the dryer shelf or other dryer surface immediately above the foam and/or overflow out of the tray. The grid structure can take any geometric shape that will fit inside the tray. A square pattern such as that used to separate vials in shipping containers would be an example. Grid wall height should be at least half the height of the tray side to preclude the interconnection of foam bubbles with adjacent bubbles as the foaming process proceeds.

In another embodiment the tray would have a cover placed over the entire area defined by the tray bottom. This cover would be located in such as way as to permit the escape of water vapor during preservation by foam formation. The tray cover could be supported by any means available to effect such support and provide the clearance necessary between the top of the tray sides and the cover bottom edge. Auxiliary posts, integral cover tabs or spacers made of any of the above materials or any similar method would accomplish the required spacing. These tray drying methods could be applied to animal health products, probiotics, food, industrial enzymes etc.

A series of experiments were conducted to investigate the feasibility of bulk drying in trays using a freeze dryer, modified for preservation by foam formation. In the first experiment, 400 ml of test solution, consisting of 50% sucrose w/w in deionized water, was filled into a stainless steel tray measuring 9½×19½×1¼ inches. The tray was placed on the middle shelf of a 3-shelf dryer. The material was then dried in accordance with the present invention. This test showed that although the tray could work as a bulk foaming container, there were problems both in containing the foam and in splashing of liquid onto adjoining surfaces during the boiling process. It was initially believed that both of these problems were serious enough to preclude the use of trays for preservation by foam formation. However, close observation showed that the foam bubbles appeared to bridge across the whole area of the tray. Consequently, it was theorized that reducing this available area would prevent the foam bubbles from growing uncontrollably.

An insert consisting of a plastic-coated cardboard material in a 1⁷⁄₁₆Δ1⁷⁄₁₆ inch grid, which had been used to separate 20 ml vials in their shipping cartons, was cut to fit inside the stainless steel tray used in the previous test. A series of experiments were conducted using the grid insert. These tests showed that the foam could be produced much more controllably and the splattering outside of the tray reduced considerably when the grid was used. However, the test material showed a pronounced tendency to stick to the tray, making removal difficult after the cycle was completed. Coating the stainless steel surface with a non-stick coating such as polytetrafluoroethylene (PTFE) may provide one solution to that problem.

In order to test this idea, a 9½×19½×2½ inch plastic tray made of high-density polyethylene (HDPE) was used. A removable HDPE insert having a 6 cell×12 cell grid and a HDPE cover was also fabricated. The recovery from the tray clearly improved. The resulting foam also hydrated easily and quickly when reconstituted. Use of the cover led to control of splattering. In addition, cell-to-cell foam uniformity was also improved within the tray. Bulk drying in trays with grids may require the removal of the material from individual grid cells on the tray. One means of facilitating this would be to fabricate a device to manually, semiautomatically or automatically hold the tray and scrape the contents out of the tray interior. This could be accomplished by separately gripping the tray and tray insert, pulling them apart and then drawing a close clearance, blade-type scraper across the exposed tray interior. The insert could be scraped clean via the application of mechanical fingers sized for close clearance to the grid cell dimensions. These fingers would be forced through the grid cells, pushing the material out of the cells onto a surface that could be further scraped clean into a collection container.

C. Formulations of Preserved Bioactive Materials in Hydrophobic Carriers

Conventional formulations of bioactive materials include dilute buffered aqueous solutions containing excipients which must be stored at low temperatures (generally 4° C. or below), or lyophilized powders or particles which must also be stored at low temperature and must be reconstituted in aqueous solutions before administration. Such formulations form degradation products using degradation pathways such as acid/base catalyzed hydrolysis, deamidation, racemization and oxidation.

Some investigators have suspended freeze-dried or spray-dried peptides and/or proteins, enzymes and nucleic acids in non-aqueous liquids, such as sesame oil or perfluorodecalin, in order to isolate the dried compounds from water. See for example, Knepp et al. WO 98/16250 and Roser et al., WO 98/41188. However, cells, viruses, vectors, and other sensitive bioactive materials which cannot be stabilized for storage at ambient and higher temperatures by conventional drying protocols, have not been dried and formulated in non-aqueous liquids. The advantages of such a formulation are that degradation processes, which occur in aqueous environments, may be minimized. Further, these non-aqueous formulations remain in a flowable form, suitable for injection and/or infusion. In addition, such formulations which contain sensitive bioactive materials that have been dried to high temperature stability by the foam formation method described herein, are particularly well adapted to storage and delivery at ambient and higher temperatures. The present invention combines the advantages associated with non-aqueous liquid formulations with the advantages associated with preservation by foam formation, e.g., scalable and adaptable to preservation of sensitive bioactive materials. The resultant formulations in accordance with one preferred mode of the present invention comprise suspensions of foam-dried, preserved preparations of viral or cellular materials that retain biological activity or viability for extended periods of time in non-aqueous vehicles, even at ambient and higher temperatures. These formulations are well suited for vaccines as well as vectors used in gene therapy and genetic engineering.

The bioactive materials are dried under conditions designed to maximize retention of biological activity. The preserved mechanically stable foams are milled as detailed above to yield uniform particulate or powdered preparations. These powders are then mixed with non-aqueous vehicles with low-reactivity, such as mineral oil, perfluorodecalin, methoxyflurane, perfluorotributylamine, cremophor-EL (polyoxyl-35-castor oil) and tetradecane. The resulting formulations are chemically and physically more stable than those formulated in aqueous solution. Vehicles such as perfluorodecalin and cremophor-EL decrease the rate of degradation since they isolate the bioactive materials from water and they lack the ability to contribute protons or other reactive moieties to degradation reactions. Such vehicles include long-chain alkanes, most preferably perfluorinated forms of alkanes.

In one aspect, the invention includes using hydrophobic vehicles such as perfluorodecalin with low reactivity to improve the overall stability of bioactive materials in a wide range of formulation conditions, including high concentrations and elevated temperatures. Consequently, shipping and/or storage of such formulations at ambient temperature and the delivery of bioactive materials in long term implantable devices become feasible. In one aspect, the present invention provides flowable pharmaceutical formulations of bioactive materials, including viral and bacterial vaccines, which exhibit the requisite preservation and long-term stability. These non-aqueous formulations comprise two components: 1) a bioactive material in a high temperature stable, substantially dry, powdered state; and 2) an anhydrous, hydrophobic, aprotic, non-polar vehicle of low reactivity and solubility power towards bioactive materials. Preferably, the dry powder form of the bioactive materials also contains stabilizers and/or other excipients. Such stabilizers and excipients are those that further reduce hydration or protect the bioactive materials from interfacial tension or other dehydration process-specific destabilization mechanisms known to those skilled in the art.

Certain nucleic acid containing compositions, such as lipid/DNA and lipid/RNA complexes, viral vectors, plasmids, cosmids, naked DNA, etc., facilitate nucleic acid uptake into cells both in vitro and in vivo. However, such complexes are inherently unstable in solution, losing most, if not all, of their activity after only a few hours to days at ambient temperatures. This feature severely limits their applicability for use in gene therapy and precludes delivery via implantable pumps, depot injection or other sustained release delivery systems where prolonged residence at 37° C. is needed. Similarly, pulmonary delivery through liquid ventilation and/or aerosolization may not be practical in aqueous solutions. Whereas, lyophilization of these nucleic acid-containing complexes results in more stable compositions, such powders require reconstitution prior to administration to render them flowable; the reconstituted solutions are not stable. The present invention provides flowable pharmaceutical formulations of nucleic acids and vectors that exhibit the requisite stability. These non-aqueous formulations comprise two components: 1) a nucleic acid containing composition in a high ambient temperature-stabilized powder formulation of low hydration; and 2) an anhydrous, hydrophobic, aprotic, non-polar vehicle of low reactivity and solubility power towards nucleic acids. The dry powder form of the nucleic acid containing composition may contain the nucleic acid in the form of lipid/DNA complexes, liposomes, ribozymes, viral vectors, virosomes, plasmids, cosmids, dendrimers, cationic polymers, PLGA particles, prokaryotic and eukaryotic cells, or the like, and preferably contain protectants and other excipients. Such stabilizers or protectants and other excipients are those that further reduce hydration or protect the bioactive materials from interfacial tension or other process-specific destabilization mechanisms known to those skilled in the art.

The formulations of the present invention are useful in a variety of delivery systems, including, but not limited to, various pumping devices (syringes, infusion sets, syringe pumps, implantable pumps, etc.), transdermal reservoir systems, liquid fill capsules, injectable depot compositions, pulmonary ventilation, instillation and/or inhalation, and the like. Applicable routes for administration of the formulations of the present invention include oral, enteral, transdermal, percutaneous, parenteral, mucosal and pulmonary delivery, all of which are known to those of skill in the art. The concentration of bioactive materials in high concentration formulations may range from at least about 1% (w/w) up to about 30% while still maintaining flowability. A preferred range is from about 10% to about 30% (w/w).

An advantage of the present invention over the prior art is that the formulations of the present invention prevent back diffusion of water vapor (and subsequent hydrolytic degradation) because the hydrophobic vehicle of the formulation acts as a barrier to water vapor. This is especially important when the formulations are used in implantable devices that must remain in an aqueous environment at elevated temperatures for long periods of time.

A further advantage of the present invention is that it allows for the formulation of bioactive materials in a flowable state at high concentrations (up to about 30% w/w). Because the bioactive material(s) is in a dry state, it is not subject to the degradation processes (e.g., aggregation, precipitation or fragmentation) observed for high concentration aqueous solutions.

An alternative formulation in accordance with the present invention comprise two components: 1) a bioactive material in a high temperature-stabilized powder of low hydration; and 2) an anhydrous, hydrophobic, low reactivity, degradable polymer. The dry powder form of the bioactive material is suspended within the degradable polymer in liquid form at a temperature high enough to maintain the polymer in the liquid state. As the suspension cools, it may be extruded to form solid cylinders, spikes, solid needles, microparticles or beads, unit dosage tablets, or any shape adapted for delivery into a mammal. The solid formulation serves the same function of maintaining the labile bioactive material in a non-aqueous environment as the liquid formulations described above. However, the solid formulation is also adapted for implantation or enteric (gastrointestinal tract) applications, where the gradual degradation of the polymer in vivo results in release of bioactive material into the aqueous environment. Any degradable polymers known to those skilled in the art which are biocompatible and degradable in biological systems may be used, including for example, polyethylene and polypropylene copolymers. Some biodegradable polymers in accordance with the present invention include polyvinyl pyrrolidone, polyethylene glycol, polyethylene oxide, polyethylene acetate, polyvinyl alcohol, polyacrylic acid, polymethacrylic acid, polyacrylamide, hydrophilic soft segment urethane, gum Arabic, gum tragacanth, and copolymeric combinations thereof. Additional preferred polymeric formulations include the bioerodible polymers disclosed in U.S. Pat. Nos. 5,849,327 and 5,968,543; the disclosures of which are incorporated herein in their entirety by reference thereto. The acrylate and methacrylate polymers sold under the tradename EUDRAGIT® (Röhm America) are also deemed useful in practice of the present invention.

Because of the relatively high temperature demands associated with suspending the preserved bioactive material in the liquid polymers, the bioactive materials are preferably vitrified with a $T_g$ above the formulation temperature. This embodiment of the present invention is particularly well suited for storage and delivery of probiotics to the gut, wherein the high temperature stabilized probiotic agents are released from the hydrophobic polymeric matrix by the action of the digestive enzymes and/or bacterial flora of the intestinal tract.

The present invention is drawn to non-aqueous formulations of dried bioactive materials with less than about 5–10% hydration suspended in hydrophobic vehicles, which formulations are stable for prolonged periods of time, even at elevated temperatures.

The bioactive materials useful in the formulations and methods of the present invention can be used in the form of a salt, preferably a pharmaceutically acceptable salt. Useful salts are known to those of skill in the art and include salts with inorganic acids, organic acids, inorganic bases or organic bases. Nucleic acids may also be complexed with lipids or be presented as liposomes, ribozymes, viral vectors, virosomes, plasmids, cosmids, dendrimers, cationic polymers, PLGA particles, prokaryotic or eukaryotic cells, or the like.

The vehicles useful in the present invention are non-aqueous, anhydrous, aprotic, non-polar, hydrophobic vehicles with low reactivity. Such vehicles have a dielectric constant less than or equal to about 15; do not contain acidic hydrogen, i.e., hydrogen attached to an oxygen or nitrogen; and generally do not solubilize or otherwise react with proteinaceous compounds. Preferred vehicles include: a) saturated hydrocarbons, b) halogenated saturated or unsaturated hydrocarbons, and c) esters and ethers of a) or b). Particularly preferred vehicles are perhalohydrocarbons and unsubstituted saturated hydrocarbons. Most preferred vehicles are biocompatible, such as perfluorodecalin, perfluorobutylamine, perfluorotripropylamine, perfluoro-N-methyldecahydroquindine, perfluoro-octohydro quinolidine, perfluoro-N-cyclohexylpyrolidine, perfluoro-N,N-dimethyl-cyclohexyl methylamine, perfluoro-dimethyl-adamantane, perfluorotri-methylbicyclo (3.3.1) nonane, bis(perfluoro-hexyl) ethene, bis(perfluorobutyl) ethene, perfluoro-1-butyl-2-hexyl ethene, tetradecane, methoxyflurane, cremophor EL (polyoxyl 35-castor oil) or mineral oil.

For pulmonary delivery, the perfluorocarbons are preferred because these liquids have a low viscosity, low surface tension, low vapor pressure, and high solubility for oxygen and carbon dioxide, making them able to promote gas exchange while in the lungs. Additional vehicles compatible with pulmonary delivery are disclosed in U.S. Pat. Nos. 5,490,498, 5,531,219 and 5,707,352; herein incorporated in their entirety by reference thereto.

The bioactive material powders useful in the present invention are solid particles wherein the hydration of the particle is less than about 5–10% (w/w water/compound). In contrast to previous formulations, where hydration and flexibility were required in order to maintain enzymatic activity, the proteins, nucleic acids, viruses, bacteria, vectors and cellular materials of the particles used in the present invention have minimal flexibility and minimal exposure to the degradative effects of moisture since hydration is minimized. The powders may be produced by milling, spray drying, spray freeze-drying, lyophilization, precipitation, and the like; however, as discussed above, preferred preservation methods involve at least primary drying of solutions or suspensions of bioactive materials in the presence of protectant molecules, like sugars, by boiling under vacuum at a temperature that is low enough to preserve the biological activity, followed by milling of the resultant mechanically-stable foam. The powders may also contain bulking agents such as glycine or mannitol that modify the morphology and/or processing characteristics of the bioactive materials, buffers that modify the pH, and non-ionic surfactants which protect from surface absorption and solubilize the bioactive materials.

Generally, the stable formulations of the present invention may be prepared by simply suspending the desired amount, which may be a therapeutically effective amount, of the desired powder containing the bioactive materials in the selected vehicle.

Such formulations are expected to retain at least a portion of their biological activity and/or viability upon rehydration following storage at ambient and elevated temperatures for greater than one month. In preferred formulations, the bioactive materials retain their activity for at least one year at 37° C. A major aspect of the invention is that the flowable non-aqueous formulations of the present invention are chemically and physically stable at high temperatures for long periods of time. Such formulations are stable even when high concentrations are used. Thus, these formulations are advantageous in that they may be shipped and stored at temperatures at or above room temperature for long periods of time. They are also suitable for administration by a variety of routes including use in implantable delivery devices and pulmonary delivery. The formulations of the present invention, which include probiotic strains of bacteria and yeast, or starter cultures, are also amenable to addition to food processing applications and as nutritional supplements.

The following Examples illustrate various specific aspects of the present invention, relating to formation of the mechanically stable porous foams, protectant materials used to enhance the preservation of sensitive viruses and bacteria, formulations of preserved dried bioactive materials in non-aqueous liquid suspensions, and various methods of scaling up production from the vial to larger bulk containers.

EXAMPLE 1

An aqueous 50% glycerol isocitrate dehydrogenase solution from Sigma Chemical Co. containing 59.4 units of activity per ml was dialyzed for 5 hours in 0.1 M TRIS HCl buffer (pH 7.4). The activity of the isocitrate dehydrogenase in the 0.1 M TRIS HCl solution after dialysis was 26±1.8 units per ml. The activity decrease was associated with a decrease in the enzyme concentration because of dilution during the dialysis.

A mixture (100 l) containing 50 l of 50% by weight sucrose solution and 50 l of the isocitrate dehydrogenase suspension in 0.1 M TRIS HCl buffer (pH 7.4) was placed in 1.5 ml plastic tubes and preserved by drying at room temperature. First, the samples were dried for 4 hours under low vacuum (0.2 atm). Second, the samples were boiled during 4 hours under high vacuum (<0.01 atm). During this step, a mechanically stable dry foam was formed in the tubes. Third, the samples were stored during 8 days over DRIERITE under vacuum at room temperature.

After 8 days, the samples were rehydrated with 500 l water. Rehydration of the samples containing dry foams was an easy process that was completed within several seconds.

The reconstituted sample was assayed for activity by assaying ability to reduce NADP, measured spectrophotometrically at 340 nm. The reaction mix included: 2 ml 0.1 M TRIS HCl buffer, pH 7.4; 10 l of 0.5% by weight NADP+; 10 l of 10 mM $MnSO_4$; 10 l of 50 mM 1-isocitrate; and 10 l of an isocitrate dehydrogenase solution. The activity was 2.6±0.2 units/ml, which means there was no loss of activity during drying and subsequent storage at room temperature.

EXAMPLE 2

A mixture (100 l) containing 50 l of 50% by weight sucrose and 50 l of an ice nucleating bacteria suspension, (INB) *Pseudomonas Syringae* ATCC 53543, were placed in 1.5 ml plastic tubes and preserved by drying at room temperature. First, the samples were dried for 4 hours under low vacuum (0.2 atm). Second, the samples were boiled during 4 hours under high vacuum (<0.01 atm). After boiling under high vacuum, a mechanically-stable porous structure was formed. Third, the samples were stored during 8 days over DRIERITE under vacuum at room temperature.

After 8 days, the samples were rehydrated with 500 l water. Rehydration of the samples containing the dry foams was an easy process that was completed within several seconds. Then the samples were assayed for ice nucleation activity in comparison with control samples. There was no significant difference between the ice nucleating activity per 1,000 bacteria in the samples preserved by the present method versus the control samples.

EXAMPLE 3

A sample containing a 1:1 mixture of a concentrated suspension of ice nucleating bacteria (INB) *Pseudomonas Syringae* ATCC 53543 and sucrose has been used. The sample was mixed until all sucrose crystals were dissolved, so that the final suspension contained 50 wt % sucrose. The suspension was placed in 20 ml vials at 2 g per vial. The vials were dried inside a vacuum chamber. The vials were sitting on the surface of a stainless steel shelf inside the chamber. The shelf temperature was controlled by circulating ethylene glycol/water antifreeze at a controlled temperature inside the shelf. Before the vacuum was applied the shelf temperature was decreased to 5 C. Then, the hydrostatic pressure inside the chamber was decreased to 0.3 Torr. Under these conditions the suspension boiled for 30 min. The temperature of the shelf was then slowly (during 30 min) increased up to 25 C. Visually stable dry foams inside the vials under these experimental conditions were formed within 3 hours. After that the samples were kept under the vacuum at room temperature for one more day. Ice nucleating activity of preserved INB was measured after the sample rehydration with 10 ml of 0.01 M phosphate buffer. Ice nucleating activity was measured as a concentration of ice nucleating centers that can nucleate an ice crystal in a 10 l buffer drop during 5 min. at −5 C. The results of the assay show ice nucleating activity in the preserved samples was equivalent to that observed in fresh controls.

EXAMPLE 4

A concentrated INB suspension was frozen to −76 C for future use. The frozen suspension (6 g) was thawed at 4 C and mixed with 4 g of 9:1 sucrose: maltrin mixture. The sample was mixed until the sugars were completely dissolved, so that the final suspension contained 35 wt % sucrose and 4 wt % maltrin. The suspension was placed inside 20 ml vials at 2 g per vial. The vials were dried inside a vacuum chamber. The vials were sitting on the surface of stainless steel shelf inside the chamber. Before the vacuum was applied the shelf temperature was decreased to 5 C. The hydrostatic pressure inside the chamber was then decreased to 0.5 Torr. Under such conditions, the suspension boiled for 30 min. The temperature of the shelf was then slowly (during 30 min) increased up to 25 C. Visually, the formation of stable dry foams inside the vials under these conditions was completed within 2.5 hours. After removal of several vials, the temperature was increased to 50 C and the remaining samples were kept under vacuum for 7 days.

Ice-nucleating activity of preserved INB was measured after the sample was rehydrated with 10 ml of 0.01 M phosphate buffer. Ice nucleating activity was measured as a concentration of ice nucleating centers that nucleate an ice crystal in a 10 μl buffer drop during 5 min at −5 C.

The ice nucleating activity of the samples that had been removed from the vacuum chamber after drying at 25 C was approximately 50% less than the initial activity of frozen-thawed INB. (The relative standard error in the measurement of ice nucleating activity is less than 20%). Because, it is known that freezing of INB does not significantly decrease ice nucleating activity, the 50% decrease of the activity observed in this experiment is probably because the additional freezing step increases sensitivity of INB to preservation by drying. At the same time, no additional decrease of the activity of the INB was observed after an additional 7 days drying at 50 C under vacuum.

EXAMPLE 5

When stable foams containing INB, prepared as above, were subjected to milling using a modified Virtis homogenizer, there was no loss of ice nucleating activity in the rehydrated powder, compared to the rehydrated foam.

EXAMPLE 6

A 60 wt % sucrose solution (1 ml) was dried in 20 ml glass vials inside a vacuum chamber. The vials were sitting on the surface of a stainless steel shelf inside the chamber. The temperature of the shelf in this experiment was kept at 20 C. The hydrostatic pressure inside the chamber was kept equal to 0.3 Torr. Under such conditions the solution slowly boiled, forming a foam consisting of thin films containing concentrated sucrose in the amorphous state. It took 2 to 3 hours to form visually stable dry foams inside the vials under these experimental conditions.

EXAMPLE 7

Freeze-dried samples of Urokinase were rehydrated with 2 ml of 40 wt % sucrose. The solutions were then transferred to 20 ml sterilized glass vials for future preservation by drying. Before drying, the vials were covered with gray slotted rubber stoppers. The vials were dried inside a vacuum chamber. The vials were sitting on the surface of a stainless steel shelf inside the chamber. Before the vacuum was applied the shelf temperature was decreased to 5 C. Then the hydrostatic pressure inside the chamber was decreased to 0.5 Torr. Under such conditions, the suspension boiled for 30 min. The temperature of the shelf was slowly increased up to 25 C during 30 min. Visually, under these experimental conditions, stable dry foams were formed inside the vials within 3 hours. After an additional 12 hours of drying at room temperature, the temperature was increased to 45 C for an additional 24 hours. After that the chamber was filled with dry $N_2$ gas, the rubber stoppers were pushed down and the vials were sealed with aluminum crimp seals.

The samples were assayed right after drying and after 30 days of storage at 40 C. After drying the Urokinase, activity was 93% of the initial activity. This decrease was associated with the loss of Urokinase during transfer from initial vials to the vials at which the Urokinase was dried. After 30 days of storage at 40 C the activity was 90%. In other words, no additional significant decrease of Urokinase activity was observed during a month of storage at 40 C.

EXAMPLE 8

Freeze-dried samples of Amphotericin B were rehydrated with 5 ml 40 wt % sucrose per vial. Then the solutions (5 ml) were transferred into 50 ml sterilized glass vials for future preservation by drying. Before drying, the vials were covered with gray butyl slotted rubber stoppers. The vials were dried inside a vacuum chamber. The vials were placed on the surface of a stainless steel shelf inside the chamber. Before the vacuum was applied the shelf temperature was decreased to 5 C. The hydrostatic pressure inside the chamber was decreased to 0.5 Torr. Under such conditions the suspension boiled for 30 min. The temperature of the shelf was then slowly (during 30 min) increased to 25 C. Visually, stable dry foams were formed inside the vials under these experimental conditions within 3 hours. After an additional 12 hours of drying at room temperature, the chamber was filled with the dry $N_2$ gas and the rubber stoppers in a portion of the vials were pushed down. The vials were removed from the chamber and subsequently sealed with aluminum crimped seal. The samples were assayed right after drying and after 30 days of storage at 27.5 and 40 C. The results are shown in Table 1, together with the results obtained in the next experiment.

Another set of freeze-dried samples of Amphotericin B was rehydrated with 5 ml 40 wt % sucrose per vial. The solutions were then transferred into sterilized glass vials for future preservation by drying similar to that described above with additional drying at 45 C for additional 24 hours. After that, the chamber was filled again with the dry $N_2$ gas, the rubber stoppers were pushed down and the vials were sealed. The samples were assayed right after drying and after 30 day of storage at 27.5 and 40 C. The results are shown in Table 1.

The decrease of Amphotericin activity right after drying was associated with the loss of Amphotericin during transformation from initial vials to the vials at which the Amphotericin was dried. The results of the assay (Table 1) suggested that the loss of potency was only detected in those samples dried at the lower temperature (25 C) and subsequently stored at 40 C.

TABLE 1

Potency of Amphotericin (%)

|  | After drying | After 30 days at 27.5 C. | After 30 days at 40 C. |
| --- | --- | --- | --- |
| Td = 25 C. | 108 | 114 | 95 |
| Td = 45 C. | 103 | 102 | 104 |
| Control | 126 | N/A | N/A |

Where Td is the maximum temperature during drying

EXAMPLE 9

A 1.5 ml tube containing a frozen (−76 C) suspension of E. coli (XL10-GOLD) from Stratagene was thawed in an ice bath. A 100 l aliquot was transferred to 50 ml of NZYM (Casein digest yeast extract medium) broth and incubated at 37 C on an orbital shaker overnight. After 14 hours of growth, 10 ml of this growth culture was inoculated into 100 ml of sterile NZYM broth to continue the culture growth at 37 C. During the culture growth the optical density (OD@620 nm) was measured every hour to determine the end of logarithmic bacteria growth. When the transition phase was reached (OD=1 to 1.06) the cells were ready to be harvested. The culture medium (5 ml) was pipetted into a centrifuge tube and centrifuged for 10 min. The supernatant was then poured off and the weight of the pellets was measured to determine the approximate concentration of the cells.

The cells were resuspended with 5 ml of NZYM broth or preservation solution consisting of 25% sucrose and 25% fructose in MRS broth. The cells resuspended with NZYM broth were used as a control. The cells suspended in 25% sucrose and 25% fructose in MRS broth (1 ml) were placed in 20 ml glass vials and dried under vacuum similar to the INB were dried in the Example 2. After that, the samples were kept under vacuum up to 24 days at room temperature. Dried samples were assayed at selected time intervals. The survival of the preserved cells was measured after rehydration with 0.1% peptone solution in water at room temperature. To determine concentration of viable cells the suspensions were pour plated in Petri dishes at the appropriate dilution on LB Miller agar followed by incubation at 37 C for 36–48 hours. Approximately 25±10% of control cells survived after drying and one day of storage under vacuum. Moreover, the portion of surviving cells did not decrease during the subsequent 24 days of storage under vacuum at room temperature.

EXAMPLE 10

Bovine Respiratory Syncytial Virus (BRSV), Rhinotracheitis (IBR), Viral Diarrhea (BVD), and Parainfluenza 3 ($PI_3$) viruses were cultured individually and harvested. After harvesting, the viruses were mixed with stabilizer and then dispensed in approximately 40 ml aliquots and then frozen in a −80° C. freezer until processing.

The following 70% w/w preservation solutions were prepared in 0.01 M phosphate buffer and sterile filtered through Corning 0.22 μm PES (Polyesthersulfone) Filter Systems: (1) 2:1 sucrose:methyl α-d-glucopyranoside, (2) 6:1 sucrose:inositol, (3) 2:1 sucrose:isomalt, (4) 5:2 sucrose: sorbitol, (5) trehalose, and (6) 5:2 sucrose:MSG.

All product preparation work was performed in an 18° C. room. Viruses were taken from the −80° C. freezer and placed in cool tap water to thaw (approximately 1 hour). Using aseptic technique, a mixture of the four viruses was prepared in a ratio set in sterile 50 ml polypropylene conical tubes. Two parts of sterile preservation solution was added to one part of viral mixture. A homogenous mixture was obtained by vortexing. For each virus/preservation solution mixture, 2.4 g was loaded into sterile 30 ml borosilicate glass serum vials (Wheaton). A sterile 13 mm finish lyophilization stopper was then placed to the first stop into the mouth of each vial, thereby leaving the notch in the stopper open to allow for water evaporation during preservation by foam formation. Vials were then place on a metal drying tray. The trays were loaded into a pre-cooled (5° C.) freeze-drier modified to execute preservation by foam formation. A thermocouple was placed in one of the vials to monitor the sample temperature during the drying process. The drying process was then performed. After preservation by foam formation was complete, vials were stoppered under vacuum and then removed from the drying machine. Vials were sealed with aluminum crimp seals and held at 4° C. The preserved samples, as well as frozen control samples, were assayed by the following methods Madin-Darby Bovine Kidney (MDBK) Cells were maintained in Dulbecco's Modified Eagle Medium (DMEM) with 5% donor horse serum (JRH Biologicals). The serum was antibody and free of BVD, IBR, $PI_3$ and BRSV. The following virus neutralizing sera were obtained from NVSL and used in the virus titration of each fraction of the vaccine: BVDV antiserum NVSL Lot 4×; $PI_3$ antiserum NVSL Lot 86.2; IBRV antiserum NVSL Lot 10×; and BRSV antiserum NVSL Lot 88-5×.

Virus titration for each fraction of the BRSV, IBR, BVD, and $PI_3$ samples was determined by a 4-way vaccine, performed by neutralizing the other three fractions with virus specific antiserum. Cultures of MDBK Cells in a 490 cm$^2$ roller bottle were removed with trypsin-EDTA (Lot #7B2028, JRH Bioscience) and suspended in DMEM+5% horse serum at 1.5×10$^5$ cells per ml. The 96-well plates were planted with the cell suspension at 200 µl per well. The microtiter plates were cultured overnight and used the next day for virus titration when the cells were about an 80% confluent monolayer.

Each vial of preserved viruses (4-way vaccine) was rehydrated with 15.5 ml of DMEM. This was considered a $10^{-0}$ dilution. The four vials of each rehydrated vaccine were pooled and used for virus titration. The control viruses were the frozen viruses. A 0.1 ml sample of the rehydrated vaccine was taken and added to a sterile 1 ml vial containing 0.3 ml of each antiserum to the other three viruses. For example, if titrating BVD, 0.1 ml of vaccine was added to a vial containing 0.3 ml anti-IBR serum, 0.3 ml anti-BRSV serum, and 0.3 ml anti-$PI_3$ serum. The total volume at this stage was 1.0 ml and the virus dilution was $10^{-1}$. The mixture was incubated for 40 minutes at room temperature.

Ten-fold dilutions of the viruses were made in 96-well plates by adding 22 µl of the neutralized ($10^{-1}$) samples to the wells (200 µl) on the first row of a plate. Each well was mixed (this was dilution $10^{-2}$) and 22 µl was transferred to the second row, and so forth until finished. Virus titrations were performed in columns 1–10. Columns 11 and 12 were left as uninfected cell controls. The plates were incubated for four days at 37° C. in a 5% $CO_2$ atmosphere. The infection of viruses was determined by cytopathic effect (CPE) readings. Finally, the virus titers were calculated by using the Reedmunch method. The titers of the four viruses obtained from the control viruses and from the preserved vaccines were recorded, and compared for loss of virus during preservation. The results are shown in Table 2; the two numbers reflect the results of duplicate experiments.

EXAMPLE 11

Newcastle and Bronchitis viruses were cultured individually and harvested. After harvesting, the viruses were mixed with stabilizer and then dispensed in approximately 200 ml aliquots and frozen at –80° C. Frozen viruses were stored in a –80° C. Revco freezer until processing.

TABLE 2

Protective Effects of Methyl α-d-Glucopyranoside and Sugar Alcohols for Preservation of BRSV, IBR, BVD and $PI_3$ Viruses

| Preservation Solution | Initial Survival (%) after Preservation | | | |
|---|---|---|---|---|
| | BRSV | IBR | BVD | $PI_3$ |
| 2:1 sucrose:methyl α-d-glucopyranoside | 57.5, 64.6 | 52.5, 37.2 | 66.1, 58.9 | 125.9, 89.1 |
| 6:1 sucrose:inositol | 38.0, 29.6 | 13.5, 10.7 | 97.7, 24.0 | 67.6, 24.0 |
| 2:1 sucrose:isomalt | 36.3, 33.9 | 16.6, 13.5 | 83.2, 9.8 | 69.2, 26.9 |
| 5:2 sucrose:sorbitol | 35.5 | 17.8 | 2.5 | 28.8 |
| Trehalose | 33.9 | 20.0 | 16.2 | 102.3 |
| 5:2 sucrose:MSG | 21.0, 29.5 | 38.0, 35.5 | 87.1, 49.0 | 91.2, 35.5 |

The following 70% w/w preservation solutions in 0.01 M phosphate buffer were prepared and sterile filtered through Corning 0.22 µm PES (Polyesthersulfone) Filter Systems: (1) 2:1 sucrose: methyl α-d-glucopyranoside, (2) 4:1 sucrose:MSG, (3) 4:1 sucrose:maltitol, and (4) 13:1 sucrose:mannitol.

All product preparation work was performed in an 18° C. room. Viruses were taken from the –80° C. freezer and placed in cool tap water to thaw (approximately 2 hours). Using aseptic technique, a mixture of the two viruses was prepared in a 1:1 ratio in sterile 50 ml polypropylene conical tubes. Two parts of preservation solution was added to one part of viral mixture. A homogenous mixture was obtained by vortexing. For each virus/preservation solution mixture, 3.0 g was loaded into sterile 30 ml borosilicate glass serum vials (Wheaton). A sterile 13 mm finish lyophilization stopper was then placed to the first stop into the mouth of each vial, thereby leaving the notch in the stopper open to allow for water evaporation during preservation by foam formation. Vials were then place on a metal drying tray. The trays were loaded into a pre-cooled (5° C.) freeze-drier modified to run the foam preservation method of the present invention. A thermocouple was placed in one of the vials to monitor the sample temperature during the drying process. After preservation, vials were stoppered under vacuum and then removed from the drying machine. Vials were sealed with aluminum crimp seals and held at room temperature or 4° C., depending on the Td of the drying run (i.e. if $T_d$=30° C., the samples were stored at room temperature; if $T_d$=20° C., the samples were held under refrigeration).

Virus titers were assayed as described above in Example 10. The results of a single experiment are shown in Table 3.

TABLE 3

Protective Effects of Methyl α-D-Glucopyranoside and Sugar Alcohols for Preservation of Newcastle and Bronchitis Viruses

| Preservation Solution | Initial Survival (%) after Preservation | |
|---|---|---|
| | Newcastle | Bronchitis |
| 2:1 sucrose:methyl α-d-glucopyranoside | 100 | 20.4 |
| 4:1 sucrose:maltitol | 56.2 | 2.4 |
| 13:1 sucrose:mannitol | 55.0 | 4.8 |
| 4:1 sucrose:MSG | 23.4 | 0.4 |

EXAMPLE 12

For preservation of *Streptococcus equi*, the following 70% w/w preservation solutions in 0.01 M phosphate buffer were prepared and sterile filtered through Corning 0.22 µm PES (Polyesthersulfone) Filter Systems: (1) 4:1 sucrose:

methyl α-d-glucopyranoside, (2) 1:1 sucrose:methyl α-d-glucopyranoside, and (3) 5:2 sucrose:glutamate.

One vial of frozen seed stock (lot WS012696) was removed from the −80° C. freezer and thawed in cold water. The entire contents (1.0 ml) were transferred to 150 ml of "S. equi growth medium" (lot 0757). According to the formula weight, 20 g of 50% Dextrose was added to the medium per liter. The flask was incubated with the cap loosened at 37° C. on the shaker set at 100 rpm for approximately 20 to 24 hours. The culture was allowed to grow until it reached an optical density (OD) of 0.8–1.5, at a wavelength of 600 nm (~12 hours). A purity streak with a loopful of the culture onto TSA II+5% blood agar (lot K1RUWW) was performed. After incubation for 24 to 48 hours at 37° C., the plate was examined and no contamination was detected.

After approximately 23.5 hours of incubation, 10 ml of the pre-culture was transferred into a 500 ml flask with 250 ml of growth medium. The pre-culture was incubated approximately 4 hours under the previously described conditions. Another purity streak onto TSA II+5% blood agar. After incubation for 24 to 48 hours at 37° C., the plate was examined and no contamination was detected. Absorbance of the pre-culture at 600 nm was 1.888.

Approximately 5 hours later, 50 ml from the second pre-culture was inoculated into the fermenter containing 1000 ml of S. equi broth+dextrose. The fermentation conditions were: aeration with pressurized oxygen at 1 liter per minute, agitation of 100 rpm, and pH regulation using 2.5 N HCL and 2.5 N NaOH at a temperature of 37° C.

Once the culture reached stationary phase, the cell culture was mixed with preservation solution in a 1:1 weight ratio. A homogenous mixture was obtained by vortexing. For each virus/preservation solution mixture, 1.0 g was loaded into sterile 10 ml borosilicate glass serum vials (Wheaton). A sterile 13 mm finish lyophilization stopper was then placed to the first stop into the mouth of each vial, thereby leaving the notch in the stopper open to allow for water evaporation during the preservation process. Vials were then place on a metal drying tray. The trays were loaded into a pre-cooled (5° C.) freeze-drier modified to execute the foam drying method. A thermocouple was placed in one of the vials to monitor the sample temperature during the drying process. After preservation, vials were stoppered under vacuum and then removed from the drying machine. Vials were sealed with aluminum crimp seals and held at room temperature.

Figure 1:
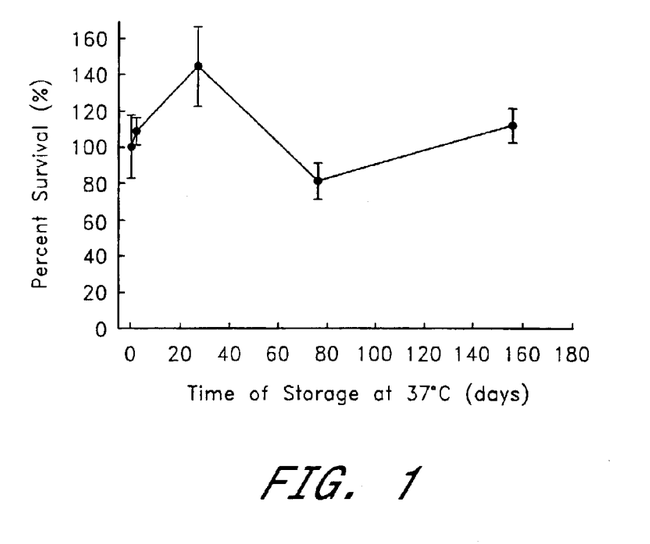
FIG. 1 shows the effects of various protectant formulations on the survival of *Streptococcus equi*.

Aliquots (1 g) of each control sample (cell culture+preservation solution) were diluted 10-fold with PBS. Sample vials from the preserved cells were rehydrated with 10 ml of PBS. The control and preserved samples were further diluted to $10^{-4}$ and $10^{-5}$. Three spread plates of $10^{-5}$ and $10^{-6}$ were prepared on blood agar. The plates were incubated at 37° C. for 48 hours. For all samples, the colonies formed on each plate were counted. The plates that yielded between 30 and 300 colonies were used to calculate the CFU/ml. The CFU/ml for the preserved samples was then divided by CFU/ml from the control samples (cell culture) to determine the % survival after preservation. The results are shown in FIG. 1.

EXAMPLE 13

A formulation of preserved L. acidophilus suspended in cottonseed oil was prepared and tested for stability. Three stir flasks each containing 200 ml of MRS broth+0.05% cysteine were each inoculated with 200 μl of frozen L. acidophilus ATCC 4356 seed culture. The stir flasks were incubated at 37° C. with gentle stirring. After 19 hours, absorbance at 600 nm and pH became stable. The cultures were pooled into one sterile 1000 ml flask.

Population control samples were performed by diluting two 1.0 ml samples of the culture in $MgCl_2/KH_2PO_4$ buffer to $10^{-6}$ and $10^{-7}$. The diluted samples were plated on MRS+cysteine agar and incubated anaerobically for 48 hours at 37° C. The balance of the culture was pipetted into three sterile 250 ml centrifuge bottles. The cells were centrifuged for 10 min at 1240×g. The supernatants were decanted off and the pellets were resuspended with 3×20 ml of $MgCl_2/KH_2PO_4$ buffer. The concentrates were pooled. A concentration control sample was taken by withdrawing 1.0 ml of the concentrate and diluting in $MgCl_2/KH_2PO_4$ buffer to $10^{-7}$ and $10^{-8}$ and plated as described above.

A preservation mixture was prepared by slowly mixing 55.0 g of re-suspended cells with 55.0 g of a 70% 5:2 sucrose:monosodium glutamate (MSG) solution dissolved in $MgCl_2/KH_2PO_4$ buffer. The mixture was vortexed and equilibrated for 30 min at room temperature. Aliquots (2×1.0 g) of the preservation mixture were diluted to $10^{-7}$ and $10^{-8}$ and plated as described above. Aliquots (50×2.0 g) of the preservation mixture were transferred into 20 ml serum vials for drying. The samples were foamed to 20° C. The shelf temperature was raised to 60° C. and the samples were further dried (secondary drying) for an additional 48 hours to a final sample temperature, $T_d$=49° C. The samples were stoppered under vacuum.

Fourteen vials were moved to a dry room (ambient r.h. ~14%). The vials were opened and the foams scraped out in to a sterile milling flask. The foams were gently milled for 30 sec. The resulting powder was weighed into 14 vials. The CFU/g was determined by re-hydrating the powder with $MgCl_2/KH_2PO_4$ buffer. The resulting cell count was divided by the dry mass of the sample.

Figure 2:
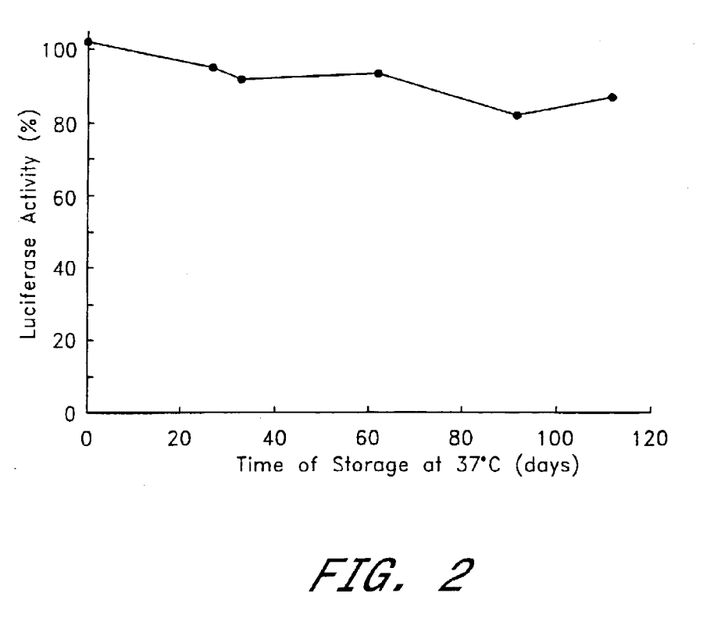
FIG. 2 illustrates viability of *Lactobacillus acidophilus* during extended storage at 37° C. as a dehydrated powder suspended in cottonseed oil.

To each of twelve vials containing the milled foam, 1000 μl of filtered, sterile de-gassed cottonseed oil was added. The vials were then stoppered with the dry ambient air and moved to a 37° C. incubator. The samples were assayed over time to determine their stability. The results are shown in FIG. 2.

EXAMPLE 14

A formulation of preserved luciferase (Sigma # L-9560) suspended in perfluorodecalin was prepared and tested for stability. Lyophilized luciferase (1 mg) was dissolved with 1 ml of 0.1 M Tris buffer, pH 7.4, containing 1 mg/ml BSA. The resulting 1 mg/ml luciferase solution was dialyzed in 500 ml of 0.1 M Tris buffer, pH 7.4, containing 1 mg/ml BSA at 4° C. for 3.5 hours. The dialyzed luciferase was transferred into a microcentrifuge tube and the luciferase concentration was determined using the following equation:

$$\text{Luciferase concentration} = \frac{\mu g \text{ of initial luciferase}}{\text{final volume of dialyzed luciferase (ml)}}$$

A preservation mixture was prepared by mixing 500 μl of 1 μg/μl dialyzed luciferase with 99.5 g of a 50% 10:1 sucrose: msg preservation solution. The preservation mixture was then weighed into nine sterile 100 ml serum vials, 10±0.05 g per vial. The remaining dialyzed luciferase was aliquoted into twenty microcentrifuge tubes, 20 μg each, and stored at −80° C. for further use as standard luciferase. The preservation mixture samples were dried to 20° C. for 4.5 hours, then to 45° C. for 60 hours, then to 60° C. for 8 hours, then to 65° C. for 16.5 hours. Samples were then stoppered under vacuum. The vials were moved to a dry room (ambient r.h. ~14%). The vials were opened and the foams scraped out in to a sterile milling flask. The foams were gently milled. The resulting powder was weighed into sterile vials, 1.07 to 1.11 g/vial. 2 ml of perfluorodecalin (Aldrich # p-990-0) was then added to each vial and the vials were stoppered with the dry ambient air and moved to a 37° C. incubator.

Luciferase assay reagent and PBS containing 1 mg/ml BSA was equilibrated at room temperature (RT) for at least 30 min. 9.42 ml of PBS containing 1 mg/ml BSA was added to a milled sample (1 µg/ml) and mixed. 1 µg/ml of this solution was used to make serial dilutions by a factor of 10 to obtain a final concentration of $1\times10^{-5}$ µg/ml. A reaction mixture was prepared by mixing 100 µl of RT luciferase assay reagent with 20 µl of diluted luciferase. The reaction mixture was placed in the luminometer and the light produced was measured every 10 seconds for 1 min. The relative light unit per second (RLU/s) versus relative enzyme concentration (µg/ml) was plotted.

Figure 3:
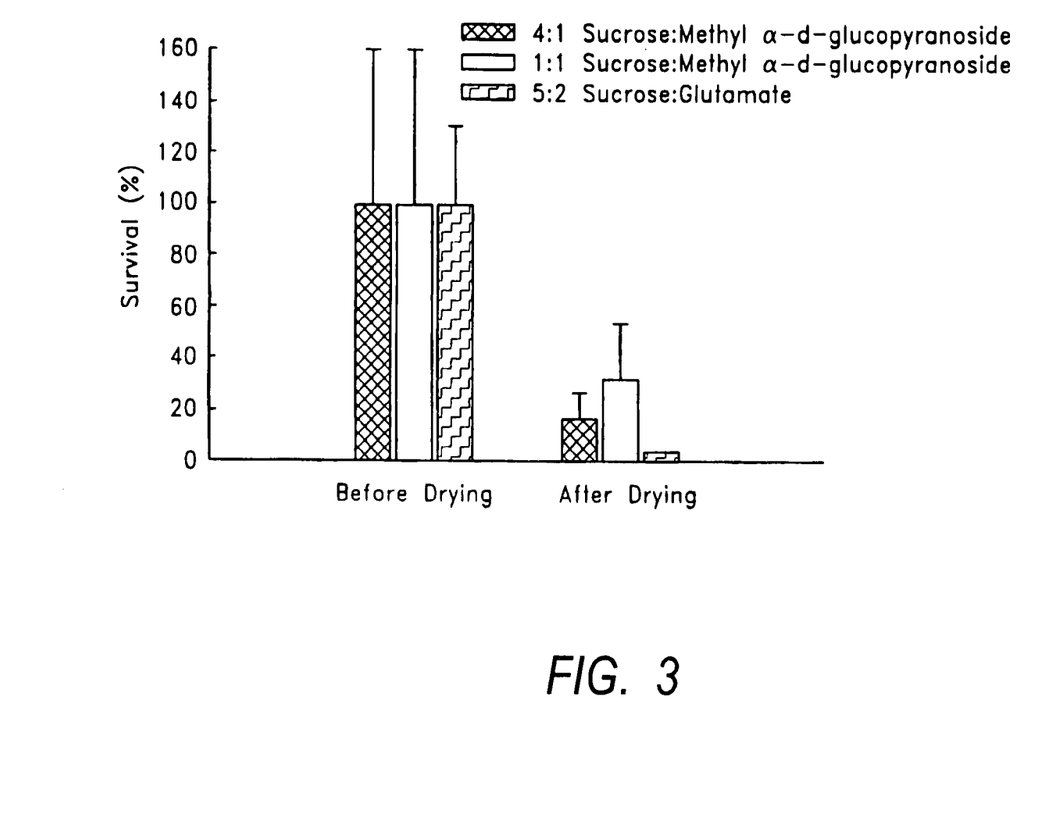
FIG. 3 shows extended stability of dehydrated luciferase in perfluorodecalin during storage at 37° C.

Each time a milled luciferase sample in perfluorodecalin was assayed, a standard luciferase sample was assayed as a control. A standard luciferase assay was performed by first dissolving 1 vial of luciferase assay substrate with 10 ml of luciferase assay buffer and equilibrated at RT for at least 30 min. Then, serial dilutions of standard luciferase were made by a factor of 10 from the original concentration to obtain a concentration in the range of $1\times10^{-5}$ µg/ml to 1 µg/ml. The reaction mixture was prepared by mixing 100 µl of RT luciferase assay reagent with 20 µl of diluted luciferase. The reaction mixture was placed in the luminometer and the light produced was measured every 10 seconds for 1 min. The relative light unit per second (RLU/s) versus relative enzyme concentration (µg/ml) was then plotted. The activity of the milled luciferase in perfluorodecalin was then compared to standard luciferase activity. The results are shown in FIG. 3.

EXAMPLE 15

Granulation of stable foams by mechanical impact of a deformable bulk container was tested. The equipment set-up consisted of a 4½ inch internal diameter glass tube connected to a standard Virtis SL600 Unitop condenser section and heated via two laboratory style hot plates from Corning. The opposite end of the glass tube was closed. A 200 ml solution of sucrose 50% w/w/in de-ionized water was introduced to a 2L PET beverage bottle, commonly used for soft drinks. This would qualify as a semi-rigid container. The bottle was placed in the tube and the sucrose solution was preserved by foam formation. After mechanically stable foam was formed, the bottle containing the foam was held overnight at 0.3 Torr and 25° C. The next morning the vacuum was broken with air. Total process time was 23 hours. Immediately following tube disassembly, the bottle was removed from the tube and purged with dry nitrogen for approximately one minute. The bottle was capped with the accompanying plastic screw top. The foam appeared to completely fill the bottle. Slight pressure applied by hand on the outside of the bottle showed the foam to be extremely brittle. Next the bottle was struck against the laboratory counter about 8–10 times with light-moderate force. All of the foam inside broke apart into discreet particles with the visual and flow characteristics of sand. A small amount of material remained adhering to the bottle interior. The glass transition temperature of the coarse particulate material was 18° C.

EXAMPLE 16

The glass tube used in Example 15 was replaced with a jacketed glass tube. The jacket was filled with water and connected to a recirculating heater bath. The bottle used previously was replaced with a 1 gallon capacity polyethylene plastic storage bag, commonly available in supermarkets. This would qualify as a flexible container. The bag was taped in place to a plastic holder to keep the bag open. The bag was filled with 150 ml of 50% w/w sucrose in de-ionized water. Primary foam drying was essentially completed 90 minutes later and the heating source switched to hot plates. Conditions at that point were 31° C. and 0.15 Torr. The foam was then held overnight. In the morning the vacuum was broken with dry nitrogen, the bag removed, purged with nitrogen for approximately 1 minute and then placed inside a Zip-Loc® 1-gallon plastic storage bag. Total process time was 71 hours. Gently crushing the bag by hand immediately reduced the foam to particles much like those produced in the bottle previously. The glass transition temperature of the resulting particles was 18.33° C.

EXAMPLE 17

The previous style bag (Example 16) was replaced with a longer, larger bag obtained from the bags used to package Petri dishes as supplied by VWR (100×15 mm size dishes). A 300 ml volume of sucrose solution, again 50% w/w in de-ionized water, was filled in the larger bag. After approximately 3 hours of primary foam drying, the heat was turned off on the circulating bath and heat supplied via the two hot plates. The next morning the hot plates were turned off (T=30° C., P=0.8 Torr) and the circulating bath set to 50° C. After about 7 hours the system temperature and pressure were 55° C. and 0.2 Torr, respectively. Total process time was 23½ hours. The system vacuum was broken with dry nitrogen, the bag removed, transferred to a 1-gallon Zip-Loc® bag and crushed gently. As before, all of the foam easily reduced to the particles like those seen previously. The glass transition temperature was 33.3° C.

EXAMPLE 18

The bacterial strain *lactobacillus acidophilus* was grown in a two liter capacity fermenter using a standard protocol specific to the species. The fermenter cell population was counted at 8.1 ∀ $0.73\times10^8$. The cells were harvested by centrifugation, resulting in 200 ml of cell concentrate with a population of 7.83 ∀$0.75\times10^9$. The cell concentrate was diluted in preservation solution consisting of 800 ml of 40% sucrose, 10% methyl α-d-glucopyranoside dissolved in 50% buffer (w/w). The resultant mixture was filled into a polyethylene Petri dish bag at 300 ml. The remainder was reserved for another use. The empty polyethylene bag was attached to a holding device located inside a 4½×19 inch, cylindrical glass chamber supported by an aluminum frame. This glass chamber served as the bulk drying chamber for preservation by foam formation. The test solution was filled into the polyethylene bag with the aid of a length of silicone tubing. The glass chamber was also fitted with an external glass water jacket along the entire tube length. The jacket was coupled to a recirculating, temperature controlled water bath. The water jacket served as the heating source for the process. The glass chamber was connected at the discharge end to the condenser of a lyophilizer. At the conclusion of the preservation by foam formation process, the system vacuum was broken with dry nitrogen. The bag was removed and examined. Dry, mechanically stable, brittle foam had clearly been produced. The material was gently crushed into particles with the consistency of sand, using light hand pressure. The bag was cut open and the contents transferred to a clean container. The container was sampled in triplicate. The container was then purged with dry nitrogen and sealed. The samples were cultured and cell populations compared to control cultures of 1 ml of dried *lactobacillus acidophilus* foam-dried in 10 ml vials by the same process. Results that demonstrate survival of the test bacterial strain are summarized in Table 4.

TABLE 4

| Sample Origin | Plate Count Mean | Plate Count Std. Dev. | Mass Assayed (g) | Volume Diluent (ml) | Activity Cell/g | Average per Sample | % Viable vs. Vial Control |
|---|---|---|---|---|---|---|---|
| Bag A | 1.21E+09 | 0.91E+07 | 0.2415 | 2.4 | 1.21E+09 | 1.12E+09 | 92.50 |
| Bag A | 1.09E+09 | 1.05E+08 | 0.3366 | 3.4 | 1.09E+09 | | 83.10 |
| Bag A | 1.07E+09 | 1.07E+08 | 0.1848 | 1.8 | 1.07E+09 | | 81.32 |

Modification of the above-described modes of carrying out various embodiments of this invention will be apparent to those of skill in the art following the teachings of this invention as set forth herein. The examples described above are not limiting, but are merely exemplary of this invention, the scope of which is defined by the following claims.

What is claimed is:

1. A vaccine formulation for ambient temperature storage and delivery of an infectious disease agent or part thereof which is sensitive to loss of activity in aqueous solution at selected ambient or higher storage temperatures, the vaccine formulation comprising:
   a powdered composition comprising the infectious disease agent or part thereof and a protectant, said powdered composition comprising solid, amorphous glass particles at the selected ambient or higher storage temperatures and said protectant comprising a methylated monosaccharide and a disaccharide; and
   a non-aqueous, non-toxic, hydrophobic vehicle, wherein the powdered composition is suspended in the vehicle at a concentration selected to yield a flowable suspension.

2. The vaccine formulation of claim 1, wherein the infectious disease agent is selected from the group consisting of a virus, a bacteria, and a parasite.

3. The vaccine formulation of claim 1, wherein at least about 20% of the activity remains stable for at least one month at 37° C.

4. The vaccine formulation of claim 1, wherein said protectant comprises methyl α-d-glucopyranoside.

5. The vaccine formulation of claim 1, wherein the hydrophobic, non-toxic vehicle is selected from the group consisting of perhalohydrocarbons, unsubstituted saturated hydrocarbons, halogenated hydrocarbons, and esters thereof.

6. The vaccine formulation of claim 5, wherein said vehicle is perfluorodecalin or cremophor EL.

7. The vaccine formulation of claim 1, wherein the powdered composition comprises up to about 50% (w/w) of the vaccine formulation.

8. A vector formulation for ambient temperature storage and delivery of a vector which is sensitive to loss of activity in aqueous solution at selected ambient or higher storage temperatures, the formulation comprising:
   a powdered composition comprising said vector and a protectant, said powdered composition comprising solid, amorphous glass particles at the selected ambient or higher storage temperatures and said protectant comprising a methylated monosaccharide and a disaccharide; and
   a hydrophobic, non-toxic vehicle, wherein the powdered composition is suspended in the vehicle at a concentration selected to yield a flowable suspension.

9. The vector formulation of claim 8, wherein at least about 20% of the activity remains stable for at least one month at 37° C.

10. The vector formulation of claim 8, wherein said protectant comprises methyl α-d-glucopyranoside.

11. The vector formulation of claim 8, wherein the hydrophobic, non-toxic vehicle is selected from the group consisting of perhalohydrocarbons, unsubstituted saturated hydrocarbons, halogenated hydrocarbons, and esters thereof.

12. The vector formulation of claim 11, wherein said vehicle is perfluorodecalin or cremophor EL.

13. The vector formulation of claim 8, wherein the powdered composition comprises up to about 50% (w/w) of the vaccine formulation.

14. A unidose formulation of a vaccine, comprising:
   a powdered composition comprising a virus or bacteria, in the form of solid, amorphous glass particles, and a protectant comprising methyl α-d-glucopyranoside; and
   a non-aqueous vehicle selected from the group consisting of perhalohydrocarbons, unsubstituted saturated hydrocarbons, halogenated hydrocarbons, and esters thereof, into which the powdered composition is suspended at a concentration selected to yield a flowable suspension, wherein the vaccine is placed in a prepackaged sterile syringe in an amount equivalent to a single effective immunizing dosage for a mammal, the vaccine being adapted to retain its activity for prolonged periods at selected ambient or higher storage temperatures.

* * * * *